US010376556B2

(12) United States Patent
Laskin et al.

(10) Patent No.: US 10,376,556 B2
(45) Date of Patent: Aug. 13, 2019

(54) METHODS AND COMPOSITIONS FOR MODULATING TRANSPORT OF A DRUG

(71) Applicants: Jeffrey D. Laskin, Piscataway, NJ (US); Ron Udasin, East Brunswick, NJ (US); Lauren Aleksunes, Bridgewater, NJ (US)

(72) Inventors: Jeffrey D. Laskin, Piscataway, NJ (US); Ron Udasin, East Brunswick, NJ (US); Lauren Aleksunes, Bridgewater, NJ (US)

( * ) Notice: Subject to any disclaimer, the term of this patent is extended or adjusted under 35 U.S.C. 154(b) by 0 days.

(21) Appl. No.: 15/845,017

(22) Filed: Dec. 18, 2017

(65) Prior Publication Data

US 2018/0104302 A1    Apr. 19, 2018

Related U.S. Application Data

(63) Continuation of application No. 15/270,439, filed on Sep. 20, 2016, now Pat. No. 9,849,155.

(51) Int. Cl.
| | | |
|---|---|---|
| *A61K 38/03* | (2006.01) | |
| *A61K 38/06* | (2006.01) | |
| *A61K 38/05* | (2006.01) | |
| *C07K 5/02* | (2006.01) | |

(52) U.S. Cl.
CPC .............. *A61K 38/05* (2013.01); *A61K 38/03* (2013.01); *A61K 38/063* (2013.01); *C07K 5/0215* (2013.01)

(58) Field of Classification Search
CPC .............. A61K 31/437; A61K 31/4985; A61K 31/519; A61K 31/704; A61K 31/7048; A61K 38/03; A61K 38/063; C07K 5/0215; C07K 5/0819
See application file for complete search history.

(56) References Cited

U.S. PATENT DOCUMENTS

| | | | |
|---|---|---|---|
| 3,984,569 A | 10/1976 | Kalopissis et al. | 514/562 |
| 6,312,734 B1 | 11/2001 | Kozhemyakin et al. | 424/617 |
| 7,943,600 B2 | 5/2011 | Froim et al. | 514/152 |
| 9,849,155 B1 | 12/2017 | Laskin et al. | |

FOREIGN PATENT DOCUMENTS

WO    WO-2017044592 A1 *  3/2017  .......... C07K 5/0806

OTHER PUBLICATIONS

Abaan et al. "Multidrug resistance mediated by MRP1 gene overexpression in breast cancer patients" Cancer Investigation 2009, 27(2):201-205.
Abe et al. "Chemosensitisation of spontaneous multidrug resistance by a 1,4-dihydropyridine analogue and verapamil in human glioma cell lines overexpressing MRP or MDR1" British journal of cancer 1995, 72(2):418-423.
Abe et al. "Possible involvement of multidrug-resistance-associated protein (MRP) gene expression in spontaneous drug resistance to vincristine, etoposide and adriamycin in human glioma cells" International journal of cancer Journal international du cancer 1994 58(6):860-864.
Aleo et al. "Endogenous thiols and Mrp transporters contribute to Hg2+ efflux in HgCl2-treated tubular MDCK cells" Toxicology 2005 206(1):137-151.
Barnouin et al. "Multidrug resistance protein-mediated transport of chlorambucil and melphalan conjugated to glutathione" British journal of cancer 1998 77(2):201-209.
Barrand et al. "A 190-kilodalton protein overexpressed in non-P-glycoprotein-containing multidrug-resistant cells and its relationship to the MRP gene" Journal of the National Cancer Institute 1994 86(2):110-117.
Benyahia et al. "Multidrug resistance-associated protein MRP1 expression in human gliomas: chemosensitization to vincristine and etoposide by indomethacin in human glioma cell lines overexpressing MRP1" Journal of neuro-oncology 2004, 66(1-2):65-70.
Brock et al. "Sequential coexpression of the multidrug resistance genes MRP and mdr1 and their products in VP-16 (etoposide)-selected H69 small cell lung cancer cells" Cancer research 1995 55(3):459-462.
Burg et al. "Inhibition of the multidrug resistance protein 1 (MRP1) by peptidomimetic glutathione-conjugate analogs" Molecular pharmacology 2002, 62(5):1160-1166.
Cheson BD & Leoni L "Bendamustine: mechanism of action and clinical data" Clinical advances in hematology & oncology : H&O 2011, 9(8 Suppl 19):1-11.

(Continued)

*Primary Examiner* — Jeffrey E. Russel
(74) *Attorney, Agent, or Firm* — Licata & Tyrrell P.C.

(57) ABSTRACT

Methods and pharmaceutical compositions for inhibiting or decreasing transport of a drug by a transporter of multidrug resistance-associated protein comprising a compound of Formula (IV)

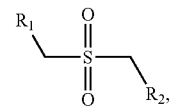

wherein $R_1$ and $R_2$ are small peptides or modified peptides, are provided. The methods and compositions are useful in enhancing efficacy of drugs such as anti-inflammatory agents, neurological agents, thyroid agents, ocular agents, cancer chemotherapeutics, antibiotics, antimicrobials, antivirals and protease inhibitors to treat human immunodeficiency virus.

13 Claims, 2 Drawing Sheets

(56) References Cited

OTHER PUBLICATIONS

Cole et al. "Overexpression of a transporter gene in a multidrug-resistant human lung cancer cell line" Science 1992, 258(5088):1650-1654.
Cullen et al. "Antibacterial prophylaxis after chemotherapy for solid tumors and lymphomas" The New England journal of medicine 2005, 353(10):988-998.
De Cremoux et al. "Role of chemotherapy resistance genes in outcome of neuroblastoma" Pediatric blood & cancer 2007, 48(3):311-317.
De Faria GP et al. "Differences in the expression pattern of P-glycoprotein and MRP1 in low-grade and high-grade gliomas" Cancer investigation 2008, 26(9):883-889.
Devault, A & Gros, P "Two members of the mouse mdr gene family confer multidrug resistance with overlapping but distinct drug specificities" Molecular and cellular biology 1990 10(4):1652-1663.
Faggad et al. "Expression of multidrug resistance-associated protein 1 in invasive ovarian carcinoma: implication for prognosis" Histopathology 2009, 54(6):657-666.
Filipits et al. "Expression of the multidrug resistance protein (MRP1) in breast cancer" Anticancer research 1999, 19(6B):5043-5049.
Filipits et al. "Clinical role of multidrug resistance protein 1 expression in chemotherapy resistance in early-stage breast cancer: the Austrian Breast and Colorectal Cancer Study Group" Journal of clinical oncology: official journal of the American Society of Clinical Oncology 2005, 23(6):1161-1168.
Gayet et al. "Transport of antimony salts by Arabidopsis thaliana protoplasts over-expressing the human multidrug resistance-associated protein 1 (MRP1/ABCC1)" FEBS letters 2006 580(30):6891-6897.
Godinot et al. "Cloning and functional characterization of the multidrug resistance-associated protein (MRP1/ABCC1) from the cynomolgus monkey" Molecular cancer therapeutics 2003 2(3):307-316.
Grant et al. "Overexpression of multidrug resistance-associated protein (MRP) increases resistance to natural product drugs" Cancer Res 1994 54(2):357-361.
Hamaguchi et al. "Cross-resistance to diverse drugs is associated with primary cisplatin resistance in ovarian cancer cell lines" Cancer research 1993 53(21):5225-5232.
Jedlitschky et al. "Transport of glutathione, glucuronate, and sulfate conjugates by the MRP gene-encoded conjugate export pump" Cancer research 1996 56(5):988-994.
Juliano et al. "A surface glycoprotein modulating drug permeability in Chinese hamster ovary cell mutants" Biochimica et biophysica acta 1976 455(1):152-162.
Kang et al. "Characteristics of human gastric carcinoma cell lines with induced multidrug resistance" Anticancer research 1997, 17(5A):3531-3536.
Keating GM, "Spotlight on rituximab in chronic lymphocytic leukemia, low-grade or follicular lymphoma, and diffuse large B-cell lymphoma" BioDrugs- : clinical immunotherapeutics, biopharmaceuticals and gene therapy 2011, 25(1):55-61.
Klaassen CD & Aleksunes LM "Xenobiotic, bile acid, and cholesterol transporters: function and regulation" Pharmacol Rev 2010, 62(1):1-96.
Kourti et al. "Expression of multidrug resistance 1 (MDR1), multidrug resistance-related protein 1 (MRP1), lung resistance protein (LRP), and breast cancer resistance protein (BCRP) genes and clinical outcome in childhood acute lymphoblastic leukemia" International journal of hematology 2007, 86(2):166-173.
Kubota et al. "Characterization of an etoposide-resistant human ovarian cancer cell line" Cancer chemotherapy and pharmacology 1994 34(3):183-190.
Leslie et al. "Transport of the beta-O-glucuronide conjugate of the tobacco-specific carcinogen 4-(methylnitrosamino)-1-(3-pyridyl)-1-butanol (NNAL) by the multidrug resistance protein 1 (MRP1). Requirement for glutathione or a non-sulfur-containing analog" The Journal of biological chemistry 2001, 276(30):27846-27854.
Leslie et al. "Arsenic transport by the human multidrug resistance protein 1 (MRP1/ABCC1). Evidence that a tri-glutathione conjugate is required" The Journal of biological chemistry 2004, 279(31):32700-32708.
Lorico et al. "Increased rate of adenosine triphosphate-dependent etoposide (VP-16) efflux in a murine leukemia cell line overexpressing the multidrug resistance-associated protein (MRP) gene" Cancer research 1995 55(19):4352-4360.
Minich et al. "The multidrug resistance protein 1 (Mrp1), but not Mrp5, mediates export of glutathione and glutathione disulfide from brain astrocytes" Journal of neurochemistry 2006 97(2):373-384.
Mookerjee Basu et al. "Inhibition of ABC transporters abolishes antimony resistance in Leishmania Infection" Antimicrobial agents and chemotherapy 2008 52(3):1080-1093.
Nicholson et al. "Combination chemotherapy in generalized Hodgkin's disease" British medical journal 1970, 3(5713):7-10.
Paumi et al. "Role of multidrug resistance protein 1 (MRP1) and glutathione S-transferase A1-1 in alkylating agent resistance. Kinetics of glutathione conjugate formation and efflux govern differential cellular sensitivity to chlorambucil versus melphalan toxicity" The Journal of biological chemistry 2001 276(11):7952-7956.
Peaston et al. "MRP1 gene expression level regulates the death and differentiation response of neuroblastoma cells" British journal of cancer 2001, 85(10):1564-1571.
Qian et al. "Glutathione stimulates sulfated estrogen transport by multidrug resistance protein 1" The Journal of biological chemistry 2001 276(9):6404-6411.
Renes et al. "Multidrug resistance protein MRP1 protects against the toxicity of the major lipid peroxidation product 4-hydroxynonenal" The Biochemical journal 2000 350 Pt 2:555-561.
Rothnie et al. "Role of GSH in estrone sulfate binding and translocation by the multidrug resistance protein 1 (MRP1/ABCC1)" The Journal of biological chemistry 2006, 281(20):13906-13914.
Rubin P: "Updated Hodgkin's disease. C. Advanced disease and special problems. Management with combination therapy" Jama 1973, 223(2):164-166.
Rush et al. "Glutathione-mediated neuroprotection against methylmercury neurotoxicity in cortical culture is dependent on MRP1" Neurotoxicology 2012 33(3):476-481.
Schneider et al. "Multidrug resistance-associated protein gene overexpression and reduced drug sensitivity of topoisomerase II in a human breast carcinoma MCF7 cell line selected for etoposide resistance" Cancer research 1994 54(1):152-158.
Smeets et al. "Idarubicin DNA intercalation is reduced by MRP1 and not Pgp" Leukemia 1999 13(9):1390-1398.
Smitherman et al. "Role of multidrug resistance protein 2 (MRP2, ABCC2) in alkylating agent detoxification: MRP2 potentiates glutathione S-transferase A1-1-mediated resistance to chlorambucil cytotoxicity" The Journal of pharmacology and experimental therapeutics 2004, 308(1):260-267.
Stride et al. "Pharmacological characterization of the murine and human orthologs of multidrug-resistance protein in transfected human embryonic kidney cells" Mol Pharmacol 1997 52(3):344-353.
Styczynski et al. "Predictive value of multidrug resistance proteins and cellular drug resistance in childhood relapsed acute lymphoblastic leukemia" Journal of cancer research and clinical oncology 2007, 133(11):875-893.
Sultana R, & Butterfield DA "Oxidatively modified GST and MRP1 in Alzheimer's disease brain: implications for accumulation of reactive lipid peroxidation products" Neurochemical research 2004 29(12):2215-2220.
Suzuki et al. "Excretion of GSSG and glutathione conjugates mediated by MRP1 and cMOAT/MRP2" Seminars in liver disease 1998 18(4):359-376.
Tada et al. "Increased expression of multidrug resistance-associated proteins in bladder cancer during clinical course and drug resistance to doxorubicin" International journal of cancer Journal international du cancer 2002, 98(4):630-635.
Tasaki et al. "Reversal by a dihydropyridine derivative of non-P-glycoprotein-mediated multidrug resistance in etoposide-resistant human prostatic cancer cell line" The Journal of urology 1995 154(3):1210-1216.

(56) References Cited

OTHER PUBLICATIONS

Tomashefsky et al. "A Combination Therapy of Mouse Sarcoma 180" Oncology 1964, 17:1-6.
Van der Bliek et al. "Genes amplified and overexpressed in human multidrug-resistant cell lines" Cancer Res 1988 48(21):5927-5932.
Van Tellingen et al. "P-glycoprotein and Mrp1 collectively protect the bone marrow from vincristine-induced toxicity in vivo" British journal of cancer 2003, 89(9):1776-1782.
Vernhet et al. "Differential sensitivities of MRP1-overexpressing lung tumor cells to cytotoxic metals" Toxicology 2000 142(2):127-134.
Wen et al. "Transgenic expression of the human MRP2 transporter reduces cisplatin accumulation and nephrotoxicity in Mrp2-null mice" Am J Pathol 2014, 184(5):1299-1308.
Wong et al. "Modulation of multidrug resistance protein 1 (MRP1/ABCC1)-mediated multidrug resistance by bivalent apigenin homodimers and their derivatives" J Med Chem 2009, 52(17):5311-5322.
Zhang et al. "Metabolism and transport of oxazaphosphorines and the clinical implications" Drug metabolism reviews 2005, 37(4):611-703.
Dirven et al. "Glutathione Conjugation of Alkylating Cytostatic Drugs with Nitrogen Mustard Group and the Role of Glutathione S-Transferase" Chemical Research in Toxicology 1996 9(2):351-360.
Gamcsik et al. "NMR Studies of the Conjugation of Mechlorethamine with Glutathione" J. Med. Chem. 1990 33:1009-1014.
Office Communication dated Apr. 10, 2017 in U.S. Appl. No. 15/270,439, filed Sep. 20, 2016.
Office Communication dated Jul. 7, 2017 in U.S. Appl. No. 15/270,439, filed Sep. 20, 2016.
Office Communication dated Sep. 28, 2017 in U.S. Appl. No. 15/270,439, filed Sep. 20, 2016.
Office Communication dated Nov. 2, 2017 in U.S. Appl. No. 15/270,439, filed Sep. 20, 2016.

\* cited by examiner

METHODS AND COMPOSITIONS FOR MODULATING TRANSPORT OF A DRUG

This application is a continuation of U.S. Ser. No. 15/270,439 filed Sep. 20, 2016, the teachings of which are incorporated herein by reference in their entirety.

This invention was made with government support under grant numbers AR055073, DK080774 and DK093903 awarded by the National Institutes of Health. The government has certain rights in this invention.

INTRODUCTION

Field of the Invention

The present invention relates to methods and compositions for modulating transport of a drug by a transporter of multidrug resistance-associated protein via administration of an agent which crosslinks glutathione in a cell or a compound comprising crosslinked small peptides or modified peptides.

Background

Efflux transporters are proteins that span the plasma membrane of a cell and catalyze the export of compounds from these cells at the expense of ATP. The first ABC transporter described was multidrug resistance protein 1 (MDR1 in human, Mdr1a/b in rodents, or P-glycoprotein; Juliano et al. *Biochimica et biophysica acta* 1976 455(1): 152-162). This 170 kilodalton transmembrane protein, encoded by the gene name ABCB1, spans the plasma membrane six times in two distinct regions (Van der Bliek et al. Cancer Res 1988 48(21):5927-5932). When this protein was first characterized, it was discovered that cells overexpressing Mdr1a/b were resistant to colchicine, doxorubicin, and actinomycin D (Devault, A & Gros, P Molecular and cellular biology 1990 10(4):1652-1663). Following the discovery of MDR1/Mdr1, it was realized that efflux pumps exist that desensitize cells to cancer chemotherapy; however, there are many cancers that do not overexpress this ATPase (Klaassen et al. Pharmacol Rev 2010 62(1):1-96). Because of this resistance of many tumors to chemotherapy, the discovery of additional xenobiotic efflux pumps was pursued, leading to the discovery and characterization of multidrug resistance-associated protein 1 (MRP1/Mrp1; Cole et al. Science 1992 258(5088):1650-1654). Soon thereafter, MRP1 was linked to resistance to anticancer drugs (Stride et al. *Mol Pharmacol* 1997 52(3):344-353; Grant et al. *Cancer Res* 1994 54(2):357-361; and Barrand et al. *Journal of the National Cancer Institute* 1994 86(2):110-117). MRP1/Mrp1 is known to transport glutathione conjugates of nitrogen mustard-derived compounds chlorambucil and melphalan (Barnouin et al. British journal of cancer 1998 77(2):201-209; Jedlitschky et al. Cancer research 1996 56(5):988-994; and Paumi et al. The Journal of biological chemistry 2001 276(11):7952-7956). Other ligands for MRP1/Mrp1 include oxidized glutathione (Minich et al. Journal of neurochemistry 2006 97(2):373-384), the topoisomerase II inhibitors doxorubicin, idarubicin (Smeets et al. Leukemia 1999 13(9):1390-1398), and etoposide (Lorico et al. Cancer research 1995 55(19):4352-4360; Tasaki et al. The Journal of urology 1995 154(3):1210-1216; Brock et al. Cancer research 1995 55(3):459-462; Abe et al. International journal of cancer Journal international du cancer 1994 58(6):860-864; Kubota et al. Cancer chemotherapy and pharmacology 1994 34(3):183-190; Schneider et al. Cancer research 1994 54(1):152-158; Hamaguchi et al. Cancer research 1993 53(21):5225-5232; Godinot et al. Molecular cancer therapeutics 2003 2(3):307-316), the lipid peroxidation product glutathione-conjugated 4-hydroxynonenal (Renes et al. The Biochemical journal 2000 350 Pt 2:555-561; Sultana R, & Butterfield D A Neurochemical research 2004 29(12):2215-2220), glutathione-conjugated aflatoxin B1, estradiol-17β-glucuronide (Qian et al. The Journal of biological chemistry 2001 276(9):6404-6411), and glutathione-conjugated methylmercury (Klaassen et al. Pharmacol Rev 2010 62(1):1-96; Rush et al. Neurotoxicology 2012 33(3):476-481; and Suzuki et al. Seminars in liver disease 1998 18(4):359-376). Some heavy metals have also been shown to act as substrates for human MRP1, including antimony salts (Gayet et al. FEBS letters 2006 580(30): 6891-6897; Mookerjee et al. Antimicrobial agents and chemotherapy 2008 52(3):1080-1093), the mercuric ion (Aleo et al. Toxicology 2005 206(1):137-151), arsenate, and arsenite (Vernhet et al. *Toxicology* 2000 142(2):127-134; Leslie et al. *The Journal of biological chemistry* 2004 279(31):32700-32708). Even for compounds transported by MRP1/Mrp1 that are not conjugated to glutathione, co-transport of glutathione, or in some cases, S-methyl glutathione (Rothnie et al. *The Journal of biological chemistry* 2006, 281(20): 13906-13914), is still required for MRP1/Mrp1 to function (Leslie et al. *The Journal of biological chemistry* 2001, 276(30):27846-27854). Nine human MRPs have been characterized; an additional MRP transporter, MRP2/Mrp2 is also known to mediate extracellular transport of glutathione-conjugated electrophiles (Klaassen C D & Aleksunes L M Pharmacol Rev 2010, 62(1):1-96). MRP2, like MRP1, has been reported to transport glutathione-conjugated chlorambucil, although less efficiently than MRP1 (Smitherman et al. *The Journal of pharmacology and experimental therapeutics* 2004, 308(1):260-267); it is also known to efflux cisplatin, a crosslinking agent with a generally similar molecular mechanism of action as the nitrogen mustard HN2 when cisplatin is conjugated to glutathione (Wen et al. Am J Pathol 2014, 184(5):1299-1308).

The human MRP1 gene was first isolated from a doxorubicin-resistant small-cell lung carcinoma, and it was determined to be a member of the ATP-binding cassette family based on its primary sequence (Cole et al. Science 1992, 258(5088):1650-1654). This transmembrane protein is overexpressed in multidrug resistant cervical cancer HeLa cells and non-small cell lung carcinoma cell lines (Cole et al. Science 1992, 258(5088):1650-1654). It has also been demonstrated that MRP1 was overexpressed in a number of human tumor cell lines that do not express MDR1 but still possess the "multidrug resistant" phenotype. Two glioma cell lines, IN500 and T98G, have elevated MRP1 expression and are resistant to etoposide, vincristine, and doxorubicin and have a decreased accumulation of etoposide following treatment (Abe et al. *International journal of cancer Journal international du cancer* 1994, 58(6):860-864; Benyahia et al. *Journal of neuro-oncology* 2004, 66(1-2):65-70). Various inhibitors of MRP1 activity were shown to reverse resistance to etoposide and doxorubicin in human glioma cells (Abe et al. British journal of cancer 1995, 72(2):418-423). Clinically, high-grade gliomas have been demonstrated to express more MRP1 than those of a lower grade (de Faria G P et al. *Cancer investigation* 2008, 26(9):883-889). Research has shown a correlation between MRP1 expression and a poor prognosis for patients with breast cancer (Filipits et al. *Anticancer research* 1999, 19(6B):5043-5049; Abaan et al. *Cancer investigation* 2009, 27(2):201-205), ovarian cancer (Faggad et al. *Histopathology* 2009, 54(6):657-666), and neuroblastoma [52-55]. Neuroblastoma cells were also shown to have an increased MRP1 expression compared to healthy cells (Peaston et al. *British journal of cancer* 2001, 85(10):1564-1571). A correlation was also shown between MRP1 expression and a poor response to treatment chemotherapy in acute lymphocytic leukemia, though this study combined several different treatment regimens, some of which included MRP1/Mrp1 substrates and some of which did not (Styczynski et al. *Journal of cancer research and clinical oncology* 2007, 133(11):875-893). A further study of acute lymphocytic lymphoma examined patients treated with the BFM-95 protocol that includes MRP1/Mrp1 ligands methotrexate, vincristine, daunorubicin, and cyclophosphamide, and a statistically significant correlation was found between MRP1 expression and poor response to therapy (Kourti et al. *International journal of hematology* 2007, 86(2):166-173). Clinical research also showed that MRP1, as well as MDR1, MRP2, and MRP3 are elevated in residual tumors following treatment with MRP1 substrate doxorubicin compared with the untreated primary tumors (Tada et al. *International journal of cancer Journal international du cancer* 2002, 98(4):630-635).

It has been suggested, as well as observed, that multiple drugs are more effective than just one compound when treating tumors. In fact, treatment with etoposide and cisplatin or chlorambucil has been the standard of care to treat B cell lymphoma for many years (Keating G M, *BioDrugs—: clinical immunotherapeutics, biopharmaceuticals and gene therapy* 2011, 25(1):55-61). The combination of cyclophosphamide, doxorubicin, vincristine, and prednisone, also known as CHOP, is commonly used and effective in combating non-Hodgkin's lymphoma (Cullen et al. *The New England journal of medicine* 2005, 353(10):988-998).

Cyclophosphamide is a nitrogen mustard-related compound that has, similar to chlorambucil and melphalan, been hypothesized to be a potential substrate for MRP1/Mrp1 once conjugated to glutathione (Zhang et al. *Drug metabolism reviews* 2005, 37(4):611-703). In fact, a correlation was observed between MRP1 expression and poor response to cyclophosphamide for breast cancer patients using this drug (Filipits et al. *Journal of clinical oncology: official journal of the American Society of Clinical Oncology* 2005, 23(6): 1161-1168). Vincristine and doxorubicin, two other compounds that are included in CHOP, are also known substrates for MRP1/Mrp1 (Abe et al. *British journal of cancer* 1995, 72(2):418-423; van Tellingen et al. *British journal of cancer* 2003, 89(9):1776-1782; de Cremoux et al. *Pediatric blood & cancer* 2007, 48(3):311-317; and Kang et al. *Anticancer research* 1997, 17(5A):3531-3536). Despite the fact that it has been known for some time that treatment with multiple cancer drugs is more efficacious than treatment with just one drug, and the impact can often be greater than an additive effect, the mechanism for such an interaction between treatments has remained elusive (Rubin P: *Jama* 1973, 223(2): 164-166; Tomashefsky et al. *Oncology* 1964, 17:1-6; and Nicholson et al. *British medical journal* 1970, 3(5713):7-10). It has long been thought that the nitrogen mustard HN2 can sensitize tumors to other cancer chemotherapeutic agents simply by causing DNA damage (Cheson B D & Leoni L: *Clinical advances in hematology & oncology: H&O* 2011, 9(8 Suppl 19):1-11).

Glutathione-conjugated electrophiles are common substrates for MRP1/Mrp1. Glutathione-conjugated ethacrynic acid derivatives have been disclosed to inhibit MRP1 in the low micromolar range (Burg et al. *Molecular pharmacology* 2002, 62(5):1160-1166). Triazole-bridged dimers have also been disclosed to be effective inhibitors of MRP1 in the nanomolar (73 to 133) range (Wong et al. *J Med Chem* 2009, 52(17):5311-5322).

SUMMARY OF THE INVENTION

An aspect of the present invention relates to a method for inhibiting or decreasing transport of a drug by a transporter of multidrug resistance-associated protein. In this method, an agent which crosslinks glutathione in a cell or a compound comprising crosslinked small peptides or modified peptides is administered to the cell thereby inhibiting or decreasing transport of a drug by a transporter of multidrug resistance-associated protein in the cell. In one nonlimiting embodiment, the method further comprises administering a drug prior to, in combination or following administration of the agent or compound. In one nonlimiting embodiment, efficacy of the drug is dependent on concentrations inside the cell. In one nonlimiting embodiment, the drug is a substrate for the transporter of multidrug resistance-associated protein.

Another aspect of the present invention relates to a method for potentiating the action of a drug on a cell. In this method, an agent which crosslinks glutathione in a cell or a compound comprising crosslinked small peptides or modified peptides is administered to the cell thereby inhibiting or decreasing transport of a drug by a transporter of multidrug resistance-associated protein in the cell. The agent or compound is administered prior to, in combination with, or following administration of a drug. In one nonlimiting embodiment, efficacy of the drug is dependent on concentrations inside the cell. In one nonlimiting embodiment, the drug is a substrate for the transporter of multidrug resistance-associated protein.

Yet another aspect of the present invention relates to a pharmaceutical composition for inhibiting or decreasing transport of a drug by a transporter of multidrug resistance-associated protein in a cell. The composition comprises an agent which crosslinks glutathione in the cell or a compound comprising crosslinked small peptides or modified peptides and a pharmaceutically acceptable carrier. In one nonlimiting embodiment, the composition further comprises a drug that is a substrate for the transporter of multidrug resistance-associated protein. In one nonlimiting embodiment, the composition further comprises a drug, efficacy of which is dependent on concentrations inside the cell.

BRIEF DESCRIPTION OF THE FIGURES

FIG. 2 is a bargraph showing the effects of HN2 on the MRP1 transporter. Bimane-GS, a fluorescent MRP1 substrate, was incorporated into inside out membrane vesicles isolated from insect cells overexpressing the MRP1 transporter. Treatment with 100 nM HN2 inhibited transporter activity. Reaction mixture containing vesicles were supplemented with 5 mM GSH.

FIG. 4A shows HEK cells overexpressing MRP1. FIG. 4B shows control cells with little or no MRP1.

DETAILED DESCRIPTION OF THE INVENTION

A large number of substrates for MRP1/Mrp1 are drugs wherein clinical efficacy is limited by MRP1-mediated efflux transport. Accordingly, pharmacological inhibition of MRP1 and other transporters of multidrug resistance-associated protein could serve as a means of increasing the sensitivity as well as specificity of such drugs.

It has now been found that agents which crosslink glutathione in a cell or compounds comprising crosslinked small peptides or modified peptides can be administered to a cell thereby inhibiting or decreasing transport of a drug by a transporter of multidrug resistance-associated protein in the cell. Accordingly, the present invention relates to compositions and methods for inhibiting or decreasing transport of a drug by a transporter of multidrug resistance-associated protein and/or potentiating the action of a drug on a cell.

By "cell" as used herein, it is meant to encompass cells in vitro, ex vivo as well as in vivo. In one nonlimiting embodiment, the cell is in a tumor in a human or other animal or is a microbe infecting a human or other animal.

By "transporter of multidrug resistance-associated protein" as used herein, it is meant to be inclusive of, but is not limited to, MRP1, MRP2, MRP3, MRP4 and MRP6.

Agents useful in the present invention must be capable of crosslinking glutathione and must be of a size and structure which does not interfere with the ability of the agent, when crosslinked with glutathione, to inhibit a transporter of multidrug resistance-associated protein. Examples of crosslinking agents useful in the present invention include, but are in no way limited to, divinyl sulfone, diethyl acetylenedicarboxylate, nitrogen mustards such as, but not limited to mechlorethamine and HN2, cisplatin and muconaldehyde. Additional crosslinking agents useful and within the scope of the present invention can be routinely selected by the skilled artisan based upon teachings herein. Nonlimiting examples of additional commercially available crosslinking agents which can be used in the present invention are disclosed in Thermo Scientific's Crosslinking Technical Handbook.

Compounds useful in the present invention comprise crosslinked small peptides or modified peptides.

By "small peptides", as used herein, it is meant a peptide of less than 20 amino acids, more preferably less than 10 amino acids and more preferably about 1 to 5 amino acid residues in length. In one nonlimiting embodiment, one or both of the small peptides is glutathione or a peptide similar in size and structure to glutathione with a nucleophilic thiol group on one end for conjugation to electrophiles. A nonlimiting example of a peptide similar in size and structure to glutathione which can be used is N-acetyl cysteine.

Nonlimiting examples of compounds useful in the present invention include wherein $R_1$ and $R_2$ are small peptides or modified peptides. As will be understood by the skilled artisan upon reading this disclosure, compounds comprising alternative crosslinking agents to those of formula (I), (II) or (III), with a size and structure which does not interfere with the ability of the compound to inhibit a transporter of multidrug resistance-associated protein, can be used and are within the scope of the present invention. Nonlimiting examples of additional commercially available crosslinking agents which could be useful in the compounds of the present invention are disclosed in Thermo Scientific's Crosslinking Technical Handbook.

In one nonlimiting embodiment, the agent or compound is administered effectively at a low concentration to inhibit or decrease transport of a drug by a transporter of multidrug resistance-associated protein and/or potentiate the action of a drug on a cell. By "low concentration" as used herein, it is meant a non-cytotoxic concentration.

In one nonlimiting embodiment, the agent or compound is co-administered with a drug. By "co-administered" as used herein, it is meant administration of the agent or compound prior to, simultaneously or subsequent to administration of the drug. In one nonlimiting embodiment, efficacy of the administered drug is dependent upon its concentrations inside a cell. In one nonlimiting embodiment, inhibiting or decreasing transport of the drug by the transporter of multidrug resistance-associated protein via coadministration of the agent or compound potentiates action of the drug on the cell. In one nonlimiting embodiment, the drug is a substrate for a transporter of multidrug resistance-associated protein. Examples of drugs which can be administered with the agents or compounds in accordance with the present invention include, but are not limited to, anti-inflammatory agents, neurological agents, thyroid agents, ocular agents, cancer chemotherapeutics, antibiotics, antimicrobials, antivirals and protease inhibitors to treat human immunodeficiency virus.

Cells to which the agents and compounds of the present invention can be administered to include, but are in no way limited to, cancer cells and microbes.

Also provided by the present invention are pharmaceutical compositions for inhibiting or decreasing transport of a drug by a transporter of multidrug resistance-associated protein in a cell. The pharmaceutical compositions of the present invention comprise an agent which crosslinks glutathione in the cell as described herein and/or a compound comprising crosslinked small peptides or modified peptides and a pharmaceutically acceptable carrier as described herein. In one nonlimiting embodiment, the pharmaceutical composition further comprises a drug. In one nonlimiting embodiment, the drug is a substrate for a transporter of multidrug resistance-associated protein. In one nonlimiting embodiment, efficacy of the drug is dependent on concentrations inside the cell. Nonlimiting examples of drugs which can be included in the present invention include anti-inflammatory agents, neurological agents, thyroid agents, ocular agents, cancer chemotherapeutics, antibiotics, antimicrobials, antivirals and protease inhibitors to treat human immunodeficiency virus.

Pharmaceutical compositions of the present invention can be administered by various routes depending upon the condition or disease to be treated. It is expected that these compositions will be effective following systemic as well as local administration. Accordingly, the pharmaceutical compositions of the invention may be administered systemically or locally, and by any suitable route such as oral, buccal, sublingual, transdermal, inhalation, subcutaneous, intraocular, intravenous, intramuscular, intrathecally, epidurally or intraperitoneal administration, and the like (e.g., by injection). Preferably, the agent which crosslinks glutathione in the cell as described herein and/or a compound comprising crosslinked small peptides or modified peptides and the drug are administered simultaneously via the same route of administration. However, it is expected that administration of the agent which crosslinks glutathione in the cell as described herein and/or the compound comprising crosslinked small peptides or modified peptides and the drug separately, via the same route or different route of administration, within a time frame during which each remains active, will also be effective therapeutically as well as in inhibiting or decreasing transport of the drug by a transporter of multidrug resistance-associated protein in cells. Further, it is expected that administration of the agent which crosslinks glutathione in the cell as described herein and/or the compound comprising crosslinked small peptides or modified peptides already receiving the drug will inhibit or decrease transport of the drug by a transporter of multidrug resistance-associated protein in cells. Thus, treatment with the agent which crosslinks glutathione in the cell as described herein and/or the compound comprising crosslinked small peptides or modified peptides and the drug need not begin at the same time. For example, administration of the agent which crosslinks glutathione in the cell as described herein and/or the compound comprising crosslinked small peptides or modified peptides may begin several days, weeks, months or more before or after treatment with the drug.

Accordingly, for purposes of the present invention, the agent which crosslinks glutathione in the cell as described herein and/or the compound comprising crosslinked small peptides or modified peptides and the drug, can be administered together in a single pharmaceutically acceptable vehicle or separately, each in their own pharmaceutically acceptable vehicle.

As used herein "pharmaceutically acceptable vehicle" includes any and all solvents, excipients, dispersion media, coatings, antibacterial and antifungal agents, isotonic and absorption delaying agents, and the like, as well as liposomes, which are compatible with the activity of the agent which crosslinks glutathione in the cell as described herein and/or the compound comprising crosslinked small peptides or modified peptides and the drug and are physiologically acceptable to a subject. An example of a pharmaceutically acceptable vehicle is buffered normal saline (0.15 M NaCl). Liposomes include water-in-oil-in-water CGF emulsions such as described in U.S. Pat. No. 5,891,468 as well as conventional liposomes. The use of such media and agents for pharmaceutically active substances is well known in the art. Except insofar as any conventional media or agent is incompatible with the agent which crosslinks glutathione in the cell as described herein and/or the compound comprising crosslinked small peptides or modified peptides or drugs, use thereof in the compositions suitable for pharmaceutical administration is contemplated. Supplementary active compounds can also be incorporated into the compositions.

Carrier or substituent moieties useful in the present invention may also include moieties which allow the agent which crosslinks glutathione in the cell as described herein and/or the compound comprising crosslinked small peptides or modified peptides and the drug to be selectively delivered to a target organ or cell. Many targeting moieties are known, and include, but are in no way limited to, asialoglycoproteins (see e.g., Wu, U.S. Pat. No. 5,166,320) and other ligands which are transported into cells via receptor-mediated endocytosis.

Solid dosage forms for oral administration include ingestible capsules, tablets, pills, lollipops, powders, granules, elixirs, suspensions, syrups, wafers, buccal tablets, troches, and the like. In such solid dosage forms the agent which crosslinks glutathione in the cell as described herein and/or the compound comprising crosslinked small peptides or modified peptides and/or the drug is mixed with at least one inert, pharmaceutically acceptable excipient or diluent or assimilable edible carrier such as, but not limited to, sodium citrate or dicalcium phosphate and/or fillers or extenders such as starches, lactose, sucrose, glucose, mannitol, and silicic acid, binders such as, for example, carboxymethylcellulose, alginates, gelatin, polyvinylpyrrolidone, sucrose, and acacia, humectants such as glycerol, disintegrating agents such as agar-agar, calcium carbonate, potato or tapioca starch, alginic acid, certain silicates, and sodium carbonate, solution retarding agents such as paraffin, absorption accelerators such as quaternary ammonium compounds, wetting agents such as, for example, cetyl alcohol and glycerol monostearate, absorbents such as kaolin and bentonite clay, and/or lubricants such as talc, calcium stearate, magnesium stearate, solid polyethylene glycols, sodium lauryl sulfate, and any mixtures thereof, or incorporated directly into a subject's diet. In the case, of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The percentage of the agent which crosslinks glutathione in the cell as described herein and/or the compound comprising crosslinked small peptides or modified peptides and/or the drug in the compositions and preparations may, of course, be varied. The amount of the agent which crosslinks glutathione in the cell as described herein and/or the compound comprising crosslinked small peptides or modified peptides and/or the drug in such therapeutically useful compositions is such that a suitable dosage will be obtained.

The solid dosage forms of tablets, dragees, capsules, pills, and granules can be prepared with coatings and shells such as enteric coatings and other coatings well-known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The agent which crosslinks glutathione in the cell as described herein and/or the compound comprising crosslinked small peptides or modified peptides and/or the drug can also be in microencapsulated form, if appropriate, with one or more of the above-mentioned excipients.

Liquid dosage forms for oral administration include pharmaceutically acceptable emulsions, solutions, suspensions, syrups and elixirs. In addition to the agent which crosslinks glutathione in the cell as described herein and/or the compound comprising crosslinked small peptides or modified peptides and/or the drug, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, ground nut corn, germ olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Suspensions, in addition to the agent which crosslinks glutathione in the cell as described herein and/or the compound comprising crosslinked small peptides or modified peptides and/or the drug, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

The pharmaceutical compositions of the present invention can be administered topically. For topical use the agent which crosslinks glutathione in the cell as described herein and/or the compound comprising crosslinked small peptides or modified peptides and/or the drug can be prepared in suitable forms to be applied to the skin, or mucus membranes of the nose and throat, and can take the form of lotions, creams, ointments, liquid sprays or inhalants, drops, tinctures, lozenges, or throat paints. Such topical formulations further can include chemical compounds such as dimethylsulfoxide (DMSO) to facilitate surface penetration of the active ingredient. In other transdermal formulations, typically in patch-delivered formulations, the pharmaceutically composition is formulated with one or more skin penetrants, such as 2-N-methyl-pyrrolidone (NMP) or Azone. For application to the eyes or ears, the compounds of the present invention can be presented in liquid or semi-liquid form formulated in hydrophobic or hydrophilic bases as ointments, creams, lotions, paints or powders.

For rectal administration, the agent which crosslinks glutathione in the cell as described herein and/or the compound comprising crosslinked small peptides or modified peptides and/or the drug can be administered in the form of suppositories admixed with conventional carriers such as cocoa butter, wax or other glyceride.

Inhalation formulations can also readily be formulated. For inhalation, various powder and liquid formulations can be prepared. For aerosol preparations, a sterile formulation of the agent which crosslinks glutathione in the cell as described herein and/or the compound comprising crosslinked small peptides or modified peptides and/or the drug may be used in inhalers, such as metered dose inhalers, and nebulizers. Aerosolized forms may be especially useful for treating respiratory disorders.

Pharmaceutical compositions according to the invention are administered at a therapeutically effective dosage sufficient to achieve the desired therapeutic effect of inhibiting or decreasing transport of the drug by a transporter of multidrug resistance-associated protein in cells. Actual dosage levels of active ingredients in the pharmaceutical compositions of this invention may be varied so as to obtain an amount of the active compound(s) that is effective to achieve the desired therapeutic response for a particular subject, compositions, and mode of administration. The selected dosage level will depend upon the activity of the particular compound, the route of administration, the severity of the condition being treated, the condition and prior medical history of the subject being treated, the age, sex, and weight of the subject, and the ability of the therapeutic compound to produce the desired therapeutic effect in the subject. Dosage regimens can be adjusted to provide the optimum therapeutic response.

The ability of various compounds of the present invention to inhibit MRP activity was demonstrated. In these experiments, the compounds divinyl sulfone, diethyl acetylenedicarboxylate, and the nitrogen mustard HN2 were demonstrated to inhibit MRP activity in A549 cells. See FIG. 1A, FIG. 1B and FIG. 1C. Treatment of A549 cells with divinyl sulfone inhibited the efflux of MRP1 substrate calcein (see FIG. 1A) with an $IC_{50}$ of 5.8 nM. Similar effects were seen following exposure to diethyl acetylenedicarboxylate (see FIG. 1B; $IC_{50}$=6.0 nM) and HN2 (see FIG. 1C, $IC_{50}$=5.5 nM).

HN2 was also demonstrated to inhibit MRP1 activity in HEK cells overexpressing MRP1. More specifically, significant inhibition of MRP1 functional activity was observed after treatment with 2 nM and 4 nM HN2. The efflux of calcein in the HEK control cells was significantly lower than that of HN2, and this background efflux was not inhibited by HN2. HN2 also inhibited efflux of calcein in HEK MRP2 cells, but 30 nM HN2 was required for significant inhibition of MRP2 function.

Figure 2:
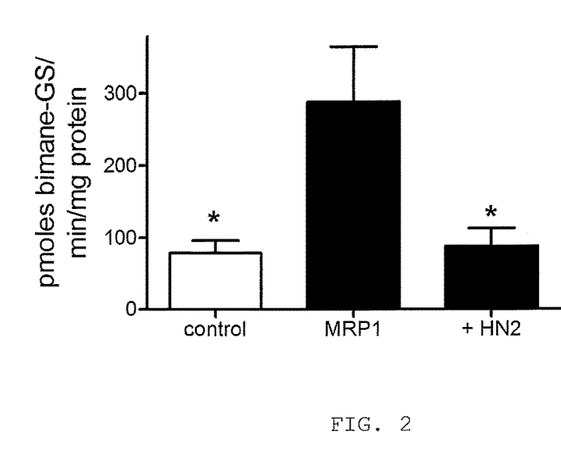

HN2 also inhibited uptake of fluorescent MRP1 substrate bimane-GS in inverted membrane vesicles prepared from Sf9 cells overexpressing human MRP1 in the nanomolar range where the assay was supplemented with 5 mM reduced glutathione to allow formation of bifunction crosslinked HN2 (see FIG. 2).

Figure 3A:
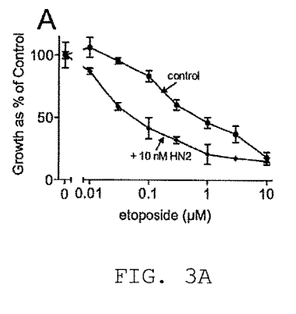
FIG. 3A through 3C are linegraphs showing the effects of HN2 on growth inhibition of A549 tumor cells by cancer chemotherapeutic agents that are substrates for MRP1. Cells were treated with non-cytotoxic concentrations of HN2 (10 nM) and increasing concentrations of etoposide (FIG. 3A), methotrexate (FIG. 3B) or vincristine (FIG. 3C). HN2, by reacting with GSH and forming a bifunctional adduct, inhibited drug efflux and markedly enhanced sensitivity to the chemotherapeutic agents.
Figure 3B:
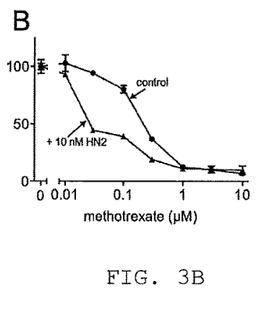
Figure 3C:
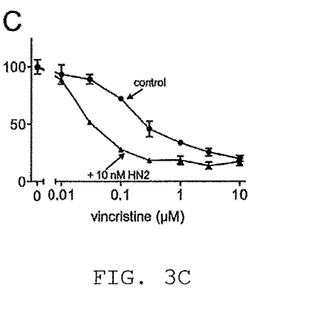

Sub-cytotoxic concentrations of HN2 were also demonstrated to sensitize tumors to another anticancer drug that can act as a substrate for MRP1. Such efficacy should prove useful in limiting the concentration used for various cancer chemotherapeutic compounds to thereby limit side effects. Specifically, it was investigated whether a sub-cytotoxic concentration of HN2 could be employed to sensitize cells to etoposide, methotrexate, or vincristine. Etoposide is an anticancer agent that causes cytotoxicity through inhibition of topoisomerase II, leading to DNA strand breaks that has long been thought to be exported from tumor cells by MRP1/Mrp1. Methotrexate is an inhibitor of dihydrofolate reductase that also is implicated as a substrate for MRP1/Mrp1. Vincristine is a microtubule-disrupting anti-mitotic compound also transported by MRP1/Mrp1. Etoposide, methotrexate or vincristine were found to inhibit growth of A549 cells (FIGS. 3A, 3B and 3C, respectively). However, co-treatment of the cells with a sub-cytotoxic concentration of HN2 (10 nM) caused significant decreases in the $IC_{50}$ for A549 cell growth inhibition, as compared with treatment with each drug in the absence of HN2 (see FIG. 3A), and these sensitizations were similar to the six-fold increase in sensitivity when treating with 25 µM MK-571, a known MRP1/mrp1 inhibitor. More specifically, treatment of cells with MRP1 ligand etoposide inhibited growth of A549 cells ($IC_{50}$=1 µM). Co-treatment with 10 nM HN2, a concentration previously determined not to induce any growth inhibition in A549 cells, sensitized the cells to etoposide in a concentration-dependent manner ($IC_{50}$=75 nM). Because HN2 does not cause any direct toxicity at this concentration, and inhibition of MRP1 functional activity is also seen (see FIG. 1), this sensitization seen after co-treatment with HN2 and etoposide is likely due to HN2 inhibiting MRP1 and the cells retaining etoposide, which increases its toxicity. It was further determined that the inhibition of calcein export by HN2 in A549 cells is reversible. Without being bound to any particular theory, these data suggest that HN2 is acting as a reversible inhibitor of MRP1 by forming a conjugate to glutathione which also acts as a substrate/inhibitor for the transporter.

HN2 also enhanced the sensitivity of A549 cells to methotrexate and vincristine. Methotrexate inhibited growth ($IC_{50}$=230 nM), and co-treatment with 10 nM HN2 enhanced this cytotoxic effect ($IC_{50}$=48 nM). Vincristine also inhibited growth of A549 cells ($IC_{50}$=360 nM), and co-treatment with 10 nM HN2 also increased vincristine-induced growth inhibition ($IC_{50}$=45 nM). Methotrexate and vincristine are also MRP1 substrates, and the concentrations of HN2 required to increase the sensitivity of A549 cells to methotrexate- and vincristine-induced growth inhibition are also concentrations experimentally determined to inhibit MRP1-mediated efflux of calcein in these cells.

HN2 (10 nM) was also effective in sensitizing HEK cells overexpressing MRP1 to etoposide-induced growth inhibition ($IC_{50}$=960 nM for etoposide alone and 42 nM cells co-treated with 10 nM HN2). HEK control cells were much more sensitive to etoposide ($IC_{50}$=55 nM), and co-treatment with 3 nM HN2 caused no change to etoposide-induced growth inhibition ($IC_{50}$=47 nM). They are more sensitive to etoposide because they do not have efflux transporters for the drug.

Accordingly, combination therapy with the nitrogen mustard HN2, as well as other crosslinking agents, and MRP1 substrates with antitumor activity can enhance the efficacy of many of these compounds when they are used to treat tumors by formation of bifunctional adducts that prevent the compounds from being effluxed from the cells. Because MRP1 has been implicated in the export of anticancer agents from tumor cells, thereby limiting their efficacy, antagonism of this efflux pump is an attractive pathway to increase the sensitivity of antitumor agents. As shown herein, the anticancer agent HN2 inhibits MRP1 functional activity at sublethal concentrations, potentially leading to a new breakthrough in understanding how to select the proper doses when using this alkylating agent in combination with other MRP1 substrates, such as etoposide, methotrexate, and vincristine.

These experiments are indicative of the crosslinking agents and compounds of the present invention also inhibiting or decreasing transport of other drugs, efficacy of which is limited by MRP1-mediated export from cells, such as, but not limited to, protease inhibitors amprenavir, ritonavir, and indinavir that are used to treat HIV/AIDS and antibiotics that act as substrates for MRP1, such as ciprofloxacin and geprafloxacin.

The following nonlimiting examples are provided to further illustrate the present invention.

EXAMPLES

Figure 1A:
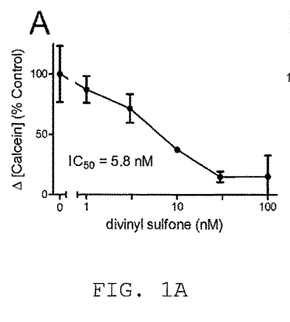
FIG. 1A through 1C are linegraphs showing inhibition of MRP1 activity in A549 tumor cells following exposure to divinyl sulfone (FIG. 1A), diethyl acetylenedicarboxylate (FIG. 1B) and the nitrogen mustard referred to herein as HN2 (FIG. 1C). In these experiments, A549 cells were treated with increasing concentrations of divinyl sulfone, diethyl acetylenedicarboxylate or HN2. Each chemical reacts in cells with glutathione (GSH) to form a bifunctional derivative. Calcein, a fluorescent MRP1 substrate, was used to measure the effects of inhibitors on MRP1 activity. Each compound inhibited MRP1 activity in A549 tumor cells in the nanomolar concentration range.
Figure 1B:
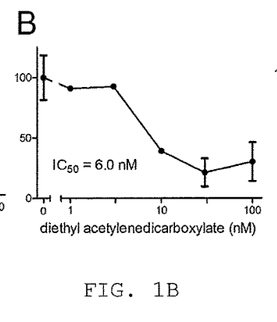
Figure 1C:
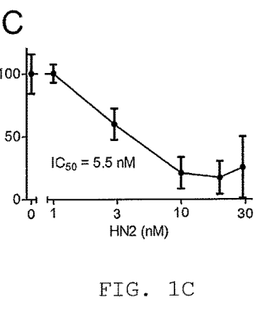

Example 1: Bifunctional Alkylating Agents Divinyl Sulfone, Diethyl Acetylenedicarboxylate and Nitrogen Mustard (HN2) Inhibit MRP1 Efflux Drug Transporter Activity in A549 Tumor Cells Bifunctional alkylating agents can form adducts with two glutathione residues. The inventors have discovered that these molecules have the capacity to inhibit drug efflux transporters. This was demonstrated in cells by showing that treatment with bifunctional alkylating agents can block efflux of substrates of the efflux transporters. For these studies, A549 lung tumor cells were used. These cells were treated with increasing concentrations of the bifunctional alkylating agents divinyl sulfone, diethyl acetylenedicarboxylate or nitrogen mustard (HN2). Each chemical can react intracellularly with glutathione to form a bifunctional derivative. Calcein, a fluorescent MRP1 substrate, was used to measure the effects of inhibitors on MRP1 activity as described by Bircsak et al. (Curr. Protoc. Toxicol. 2013 57, Unit 23 6). After treatment with a bifunctional alkylating agent, each compound was found to inhibit calcein efflux from A549 cells in the nanomolar concentration range and in a concentration-dependent manner. See FIG. 1A showing divinyl sulfone inhibits MRP1-mediated calcein efflux from A549 cells; FIG. 1B showing diethyl acetylenecarboxylate inhibits MRP1-mediated calcein efflux from A549 cells; and FIG. 1C showing nitrogen mustard (HN2) inhibits MRP1-mediated calcein efflux from A549 cells. The error bars represent the means±SE, n=3.

Example 2: Effects of HN2 on the MRP1 Transporter

Bifunctional alkylating agents that have reacted with glutathione were also shown to directly inhibit a cloned recombinant efflux transporter. In these studies, inside-out plasma membrane vesicles containing recombinant MRP1 accumulate the fluorescent efflux transporter substrate, glutathionyl bimane (bimane-GS). Treatment of the efflux transporter with a glutathione bifunctional adduct blocks the accumulation of the efflux transporter substrate. Bimane-GS was used to monitor MRP1 functional activity in inverted membrane vesicles as disclosed by Idasher et al. (Toxicology 2013, 306:108-113). More specifically, inside-out Sf9 insect cell plasma membrane vesicles expressing human MRP1 and those transfected with an empty vector (control) were purchased from Sigma-Aldrich (St. Louis, Mo.). To assess the ability of HN2 to inhibit MRP1-mediated transport of bimane-GS, 20 mg vesicles were incubated with 10 µM bimane-GS, 4 mM adenosine triphosphate, 5 mM reduced glutathione, and 100 nM HN2 in reaction buffer at 37° C. for 10 minutes according to the manufacturer's protocol. Vesicles were washed, vacuum filtered, and solubilized with 50% methanol. Fluorescence was read at excitation wavelength 430 nm and emission wavelength 538 nm. Results are shown in FIG. 2. The control (open bar) shows low uptake of bimane-GS in vesicles that did not contain the MRP1 efflux transporter. Vesicles containing the MRP1 transporter (center filled in bar) readily take up bimane-GS. Uptake of bimane-GS was blocked in vesicles containing the MRP1 transporter (right filled in bar) treated with the bifunctional alkylating agent, nitrogen mustard (HN2). The error bars represent the means±SE, n=3. The asterisks indicate that the bars are significantly different than vesicles containing MRP1 and not treated with HN2 (student t test).

Example 3: Ability of Nitrogen Mustard (HN2) to Enhance Growth Inhibition of A549 Tumor Cells by Cancer Chemotherapeutic Agents Known to Efflux Via MRP1 Transporters

Many anticancer agents are limited in their effectiveness as they are substrates for the MRP1 drug efflux transporter and removed from cancer cells. Findings disclosed herein that bifunctional alkylating agents modified with glutathione can effectively block the MRP1 efflux transporter are indicative that they would have the capacity to enhance the activity of chemotherapeutic agents that are MRP1 substrates by retaining them in the cancer cells. A549 lung tumor cells were used to demonstrate that a bifunctional alkylating agent (nitrogen mustard, HN2) can enhance cancer drug cytotoxicity as measured by growth inhibition. In these studies, A549 lung tumor cells were treated with non-cytotoxic concentrations of HN2 (10 nM) and increasing concentrations of the drugs etoposide, methotrexate or vincristine, each of which is known to be a substrate of MRP1. HN2, by reacting with intracellular glutathione (GSH) and forming bifunctional GSH adducts, inhibits efflux of the drugs and markedly enhances their sensitivity to etoposide, methotrexate or vincristine. Thus, lower concentrations of the drugs are able to inhibit cell growth in cells pretreated with HN2, which blocked the MRP1 efflux transporter, when compared to cells not treated with HN2. In these experiments, growth inhibition was measured as described by Udasin et al. (Toxicological sciences: an official journal of the Society of Toxicology 2015), Mariano et al. (Biochemical pharmacology 2002, 63(1):31-39), and Martey et al. (Biochem Pharmacol 2002, 63(11):2001-2009). A549 cells were plated at low density (1.8-3.0×$10^4$ cells/well) in 24-well tissue culture dishes in growth medium and allowed to adhere overnight. The medium was then replaced with 0.35 mL of serum-free growth medium supplemented with 10 nM HN2 or control. After 1 hour, cells were then treated with increasing concentrations of etoposide, methotrexate or vincristine. Thirty minutes later, the cells were washed twice with HBSS and refed with fresh drug-free growth medium. After an additional 72 hours, cells were removed from the dishes with trypsin and counted using a Z1 Coulter Particle Counter (Beckman Coulter, Brea, Calif.). FIG. 3A shows that HN2 markedly enhanced growth inhibition of cells treated with etoposide. FIG. 3B shows that HN2 markedly enhanced growth inhibition of cells treated with methotrexate. FIG. 3C shows that HN2 markedly enhanced growth inhibition of cells treated with vincristine. The error bars represent the means±SE, n=3.

Example 4: Ability of Nitrogen Mustard (HN2) to Enhance Etoposide-induced Growth Inhibition in HEK Cells Expressing MRP1

Figure 4A:
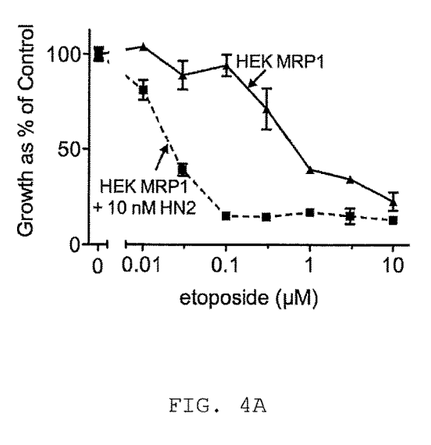
FIG. 4A and FIG. 4B are linegraphs showing the effects of etoposide on HN2-induced growth inhibition in HEK cells overexpressing MRP1. Cells were treated with non-cytotoxic concentrations of HN2 (10 nM), followed by increasing concentrations of etoposide. Initial treatment with HN2 blocked the MRP1 efflux transporter in HEK cells overexpressing MRP1 (HEK MRP1) and increased their sensitivity to further treatments with HN2.
Figure 4B:
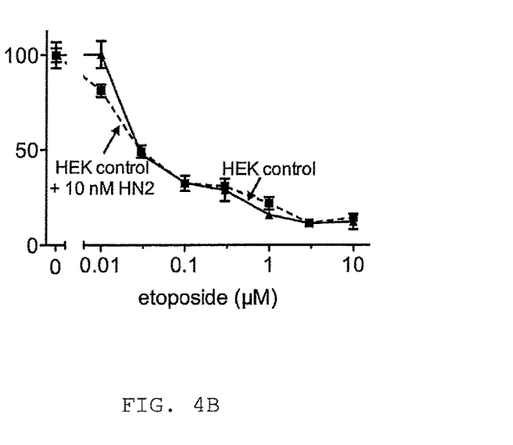

Human embryonic kidney 293 (HEK) cells stably transfected to overexpress MRP1 (HEK MRP1) and those transfected with an empty pcDNA 3 vector (HEK control) and thus do not express MRP1 (HEK) were used as described by Robey et al. (British journal of cancer 2003 89(10):1971-1978 and Journal of pharmacological and toxicological methods 2011 63(3):217-222). Cells were treated with non-cytotoxic concentrations of HN2 (10 nM) and increasing concentrations of the drug, etoposide. HN2, by reacting with intracellular GSH and forming bifunctional adducts, inhibits MRP1-mediated efflux of etoposide and markedly increases sensitivity to this chemotherapeutic agent in HEK-MRP1 cells. Thus, lower concentrations of etoposide are able to inhibit cell growth. In contrast, HN2 does not enhance sensitivity of HEK cells to etoposide since they express little or no MRP1 transporter. In these experiments, growth inhibition was measured as described in Example 3. HEK and HEK-MRP1 cells were plated at low density (1.8-3.0× $10^4$ cells/well) in 24-well tissue culture dishes in growth medium and allowed to adhere overnight. The medium was then replaced with 0.35 mL of serum-free growth medium supplemented with 10 nM HN2 or control. After 1 hour, cells were then treated with increasing concentrations of etoposide. Thirty minutes later, the cell culture medium was supplemented with fetal bovine serum to a final concentration of 10%. After an additional 72 hours, cells were removed from the dishes with trypsin and counted using a Z1 Coulter Particle Counter (Beckman Coulter, Brea, Calif.). FIG. 4A shows HEK cells overexpressing MRP1 while FIG. 4B shows control cells with little or no MRP1. Initial treatment with HN2 blocked the MRP1 efflux transporter in HEK cells overexpressing MRP1 (HEK MRP1) and increased their sensitivity to further treatments with HN2. The error bars represent the means±SE, n=3.

What is claimed is:

1. A method for inhibiting or decreasing transport of a drug by a transporter of multidrug resistance-associated protein in a cell, said method comprising administering to the cell a compound of Formula (IV)

wherein $R_1$ and $R_2$ are small peptides or modified peptides; and wherein the cell is a microbe.

2. The method of claim 1 wherein $R_1$ or $R_2$ comprise glutathione.

3. The method of claim 1 wherein $R_1$ and $R_2$ comprise glutathione.

4. The method of claim 1 wherein efficacy of the drug is dependent on concentrations inside the cell.

5. The method of claim 1 wherein inhibiting or decreasing transport of the drug by the transporter of multidrug resistance-associated protein potentiates action of the drug on the cell.

6. A method for inhibiting or decreasing transport of a drug by a transporter of multidrug resistance-associated protein in a cell, said method comprising administering to the cell a drug that is a substrate for the transporter of multidrug resistance-associated protein and a compound of Formula (IV)

wherein $R_1$ and $R_2$ are small peptides or modified peptides.

7. The method of claim 6 wherein the drug is selected from the group consisting of anti-inflammatory agents, neurological agents, thyroid agents, ocular agents, cancer chemotherapeutics, antibiotics, antimicrobials, antivirals and protease inhibitors to treat human immunodeficiency virus.

8. The method of claim 6 wherein the cell is a cancer cell.

9. A pharmaceutical composition for inhibiting or decreasing transport of a drug by a transporter of multidrug resistance-associated protein in a cell, said composition comprising a compound of Formula (IV)

wherein $R_1$ and $R_2$ are small peptides or modified peptides, a drug that is a substrate for the transporter of multidrug resistance-associated protein, and a pharmaceutically acceptable carrier.

10. The pharmaceutical composition of claim 9 wherein $R_1$ or $R_2$ comprise glutathione.

11. The pharmaceutical composition of claim 9 wherein $R_1$ and $R_2$ comprise glutathione.

12. The pharmaceutical composition of claim 9 wherein efficacy of the drug is dependent on concentrations inside the cell.

13. The pharmaceutical composition of claim 9 further comprising a drug selected from the group consisting of anti-inflammatory agents, neurological agents, thyroid agents, ocular agents, cancer chemotherapeutics, antibiotics, antimicrobials, antivirals and protease inhibitors to treat human immunodeficiency virus.

* * * * *